US008753332B2

(12) United States Patent
Bragagna et al.

(10) Patent No.: US 8,753,332 B2
(45) Date of Patent: Jun. 17, 2014

(54) LASER DEVICE AND METHOD FOR ABLATING BIOLOGICAL TISSUE

(75) Inventors: Thomas Bragagna, Feldkirch (AT); Arne Heinrich, Feldkirch (AT); Simon Gross, Altach (AT)

(73) Assignee: Pantec Biosolutions AG, Ruggell (LI)

( * ) Notice: Subject to any disclaimer, the term of this patent is extended or adjusted under 35 U.S.C. 154(b) by 444 days.

(21) Appl. No.: 12/682,964

(22) PCT Filed: Oct. 27, 2008

(86) PCT No.: PCT/EP2008/064560
§ 371 (c)(1),
(2), (4) Date: Jun. 29, 2010

(87) PCT Pub. No.: WO2009/053499
PCT Pub. Date: Apr. 30, 2009

(65) Prior Publication Data
US 2010/0292680 A1    Nov. 18, 2010

(30) Foreign Application Priority Data

Oct. 25, 2007  (EP) .................. PCT/EP2007/061503
Oct. 27, 2008  (EP) .................. PCT/EP2008/064560

(51) Int. Cl.
A61B 18/20    (2006.01)
(52) U.S. Cl.
CPC ..................... A61B 18/20 (2013.01)
USPC ............................................... 606/13
(58) Field of Classification Search
CPC ........................................ A61B 18/20
USPC .............................................. 606/13
See application file for complete search history.

(56) References Cited

U.S. PATENT DOCUMENTS 4,705,037 A  * 11/1987  Peyman et al. ............... 606/166
4,718,417 A  *  1/1988  Kittrell et al. ................... 606/7
(Continued)

FOREIGN PATENT DOCUMENTS

GB          2415387 A  * 12/2005  ............... A61N 5/06
WO    WO 9409713 A1  *  5/1994  ............. A61B 17/36
(Continued)

OTHER PUBLICATIONS

P. J. Caspers et al., Automated depth-scanning confocal Raman microspectrometer for rapid in vivo determination of water concentration profiles in human skin, J. Raman Spectrosc. 31, 813-818 (2000).*

(Continued)

Primary Examiner — Bill Thomson
Assistant Examiner — Manolis Pahakis
(74) Attorney, Agent, or Firm — Fish & Associates, PC

(57) ABSTRACT

A laser device (10) for ablating a biological tissue (1), comprising: a) a laser source (7) that is configured to emit a laser beam (4); b) optics (8a, 8b, 8x) configured to modify the laser beam (4) such as to direct the laser beam (4) on the biological tissue (1); d) a controller (11) that is configured to control the laser source (7) to emit the laser beam (4) to create an ablation in biological tissue (1), whereby e) a sensor (19) being configured to receive back scattered light from the biological tissue (1); f) a tissue controller (18) that is operationally coupled to the sensor (19) to receive a sensor signal (Ri) of the sensor (19); and g) the tissue controller (18) being configured to compare a series of at least two consecutive sensor signals (R1, R2, R3, . . . ) and being configured to generate a tissue control signal (TCS) when the value of the series of consecutive sensor signals (R1, R2, R3, . . . ) decreases in a predetermined amount.

12 Claims, 6 Drawing Sheets

(56) References Cited

U.S. PATENT DOCUMENTS

| | | | |
|---|---|---|---|
| 4,775,361 A * | 10/1988 | Jacques et al. | 604/20 |
| 4,887,605 A * | 12/1989 | Angelsen et al. | 600/439 |
| 4,939,336 A * | 7/1990 | Meyer et al. | 219/121.62 |
| 5,219,345 A * | 6/1993 | Potter | 606/15 |
| 5,290,273 A * | 3/1994 | Tan | 606/9 |
| 5,360,447 A * | 11/1994 | Koop | 128/898 |
| 5,423,803 A * | 6/1995 | Tankovich et al. | 606/9 |
| 5,460,182 A * | 10/1995 | Goodman et al. | 600/342 |
| 5,501,680 A * | 3/1996 | Kurtz et al. | 606/9 |
| 5,554,153 A * | 9/1996 | Costello et al. | 606/9 |
| 5,586,981 A * | 12/1996 | Hu | 606/9 |
| 5,628,744 A | 5/1997 | Coleman et al. | |
| 5,643,252 A * | 7/1997 | Waner et al. | 606/9 |
| 5,658,323 A * | 8/1997 | Miller | 607/89 |
| 5,720,894 A * | 2/1998 | Neev et al. | 216/65 |
| 5,839,446 A * | 11/1998 | Waner et al. | 128/898 |
| 5,879,346 A * | 3/1999 | Waldman et al. | 606/9 |
| 5,885,211 A * | 3/1999 | Eppstein et al. | 600/309 |
| 5,928,222 A * | 7/1999 | Kleinerman | 606/16 |
| 6,027,496 A * | 2/2000 | Loomis et al. | 606/9 |
| 6,056,738 A * | 5/2000 | Marchitto et al. | 606/2 |
| 6,063,108 A * | 5/2000 | Salansky et al. | 607/89 |
| 6,074,382 A * | 6/2000 | Asah et al. | 606/9 |
| 6,142,939 A * | 11/2000 | Eppstein et al. | 600/309 |
| 6,165,170 A * | 12/2000 | Wynne et al. | 606/9 |
| 6,168,590 B1 * | 1/2001 | Neev | 606/9 |
| 6,208,458 B1 * | 3/2001 | Galvanauskas et al. | 359/345 |
| 6,245,060 B1 * | 6/2001 | Loomis et al. | 606/9 |
| 6,275,726 B1 * | 8/2001 | Chan et al. | 600/476 |
| 6,299,307 B1 * | 10/2001 | Oltean et al. | 351/210 |
| 6,315,772 B1 * | 11/2001 | Marchitto et al. | 606/9 |
| 6,328,733 B1 * | 12/2001 | Trost | 606/13 |
| 6,355,054 B1 * | 3/2002 | Neuberger | 607/89 |
| 6,383,177 B1 * | 5/2002 | Balle-Petersen et al. | 606/9 |
| 6,385,221 B1 * | 5/2002 | Neuberger | 372/38.02 |
| 6,387,059 B1 * | 5/2002 | Marchitto et al. | 600/473 |
| 6,387,089 B1 * | 5/2002 | Kreindel et al. | 606/9 |
| 6,413,267 B1 * | 7/2002 | Dumoulin-White et al. | 607/89 |
| 6,423,055 B1 * | 7/2002 | Farr et al. | 606/15 |
| 6,447,503 B1 * | 9/2002 | Wynne et al. | 606/9 |
| 6,494,900 B1 * | 12/2002 | Salansky et al. | 607/89 |
| 6,527,716 B1 * | 3/2003 | Eppstein | 600/309 |
| 6,613,040 B2 * | 9/2003 | Tankovich et al. | 606/3 |
| 6,663,659 B2 * | 12/2003 | McDaniel | 607/88 |
| 6,676,654 B1 * | 1/2004 | Balle-Petersen et al. | 606/9 |
| 6,676,655 B2 * | 1/2004 | McDaniel | 606/9 |
| 6,692,456 B1 * | 2/2004 | Eppstein et al. | 604/22 |
| 6,866,678 B2 * | 3/2005 | Shenderova et al. | 607/88 |
| 7,112,194 B2 * | 9/2006 | Fujieda | 606/10 |
| 7,115,120 B2 * | 10/2006 | Lin | 606/4 |
| 7,184,614 B2 * | 2/2007 | Slatkine | 385/5 |
| 7,309,335 B2 * | 12/2007 | Altshuler et al. | 606/11 |
| 7,353,829 B1 * | 4/2008 | Wachter et al. | 128/898 |
| 7,730,893 B2 * | 6/2010 | Dougal | 128/898 |
| 7,758,561 B2 * | 7/2010 | Eppstein | 604/500 |
| 8,435,791 B2 * | 5/2013 | Galun et al. | 435/460 |
| 2002/0133147 A1 * | 9/2002 | Marchitto et al. | 606/9 |
| 2002/0169394 A1 * | 11/2002 | Eppstein et al. | 600/573 |
| 2002/0183729 A1 * | 12/2002 | Farr et al. | 606/15 |
| 2003/0078499 A1 * | 4/2003 | Eppstein | 600/439 |
| 2003/0092982 A1 * | 5/2003 | Eppstein | 600/411 |
| 2004/0039342 A1 * | 2/2004 | Eppstein et al. | 604/200 |
| 2004/0053491 A1 | 3/2004 | Park | |
| 2004/0092913 A1 * | 5/2004 | Hennings et al. | 606/3 |
| 2004/0098070 A1 * | 5/2004 | Mohr et al. | 607/89 |
| 2004/0102764 A1 * | 5/2004 | Balling | 606/5 |
| 2005/0049582 A1 * | 3/2005 | DeBenedictis et al. | 606/9 |
| 2006/0217594 A1 * | 9/2006 | Ferguson | 600/175 |
| 2007/0016074 A1 * | 1/2007 | Abreu | 600/475 |
| 2007/0032781 A1 * | 2/2007 | Henry et al. | 606/9 |
| 2007/0088208 A1 * | 4/2007 | Yasuzawa et al. | 600/345 |
| 2007/0129778 A1 * | 6/2007 | Dougal | 607/88 |
| 2007/0219605 A1 * | 9/2007 | Yaroslavsky et al. | 607/100 |
| 2008/0058782 A1 * | 3/2008 | Frangineas et al. | 606/9 |
| 2008/0195085 A1 * | 8/2008 | Loeb | 606/3 |
| 2008/0208104 A1 * | 8/2008 | Bragagna et al. | 604/20 |
| 2008/0255034 A1 * | 10/2008 | Bohler et al. | 514/8 |
| 2008/0306471 A1 * | 12/2008 | Altshuler et al. | 606/10 |
| 2009/0012508 A1 * | 1/2009 | Dougal | 606/9 |
| 2009/0299262 A1 * | 12/2009 | Bragagna et al. | 604/20 |
| 2009/0306576 A1 * | 12/2009 | Bragagna et al. | 604/20 |
| 2010/0016688 A1 * | 1/2010 | Debreczeny et al. | 600/310 |
| 2010/0049117 A1 * | 2/2010 | Bragagna et al. | 604/20 |

FOREIGN PATENT DOCUMENTS

| | | | |
|---|---|---|---|
| WO | 2002/089688 | 11/2002 | |
| WO | WO 2006111201 A1 * | 10/2006 | A61B 18/20 |
| WO | WO 2006111526 A1 * | 10/2006 | |

OTHER PUBLICATIONS

Caspers et al., Combined In Vivo Confocal Raman Spectroscopy and Confocal Microscopy of Human Skin, Biophysical Journal, vol. 85, Jul. 2003, 572-580.*

Caspers et al., In Vivo Confocal Raman Microspectroscopy of the Skin: Noninvasive Determination of Molecular Concentration Profiles, J Invest Dermatol 116:434-442, 2001.*

* cited by examiner

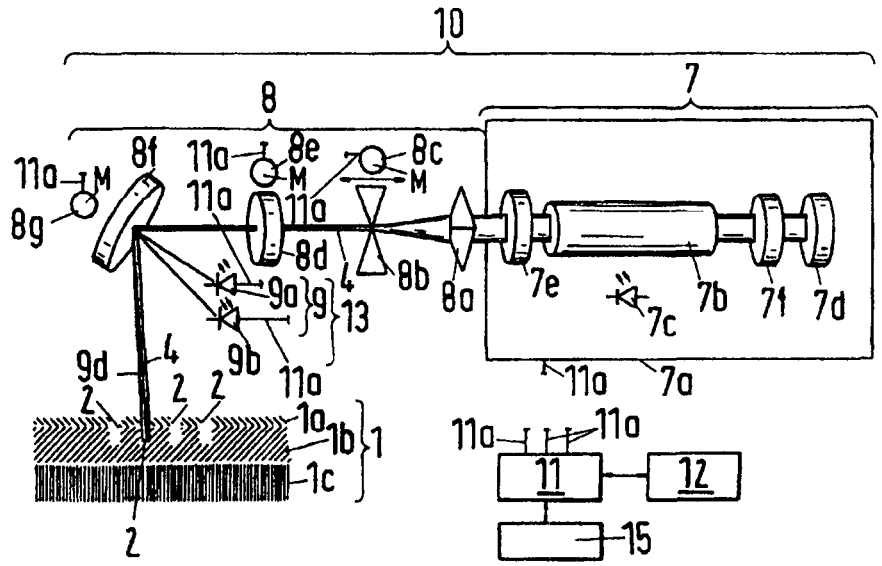

LASER DEVICE AND METHOD FOR ABLATING BIOLOGICAL TISSUE

FIELD OF THE INVENTION

This invention relates to a laser device and a method for ablating biological tissue.

BACKGROUND OF THE INVENTION

Document WO2006/111526 of the same applicant discloses a laser porator for creating micropores in a biological tissue such as the skin. This laser porator comprises a feedback mechanism to analyze a characteristic of a pore. One disadvantage of this laser porator is that the feedback mechanism is not reliable enough to easily and quickly distinguish different properties of tissues. Document WO2006/111526 is herewith incorporated by reference in its entirety.

U.S. Pat. No. 5,628,744 discloses a treatment beam handpiece which allows to differentiate between normal skin tissue and a lesion. The handpiece comprises a treatment beam and a probe beam. The reflectance of the probe beam allows to distinguish the normal skin tissue and the lesion, so that the treatment beam may be activated only when there is a lesion. This handpiece has the disadvantage that it is not able to analyze a characteristic of inside the pore. The handpiece is only able to distinguish the surface of the skin.

It is therefore an object of the present invention to provide devices and methods to improve the recognition of tissue properties, in particular to detect different tissue layers below the surface of the skin. It is a further object of the present invention to provide an inexpensive and reliable device and method for tissue ablation.

SUMMARY OF THE INVENTION

This problem is solved with the features claimed below.

The problem is in particular solved with a laser device for ablating a biological tissue, comprising:
a) a laser source that is configured to emit a laser beam;
b) optics configured to modify the laser beam such as to direct the laser beam on the biological tissue;
d) a controller that is configured to control the laser source to emit the laser beam to create an ablation in biological tissue, wherein
e) a sensor is configured to receive back scattered light from the biological tissue, most preferably from within a pore in the skin;
f) a tissue controller is operationally coupled to the sensor to receive a sensor signal of the sensor; and
g) wherein the tissue controller being configured to compare a series of at least two consecutive sensor signals and being configured to generate a tissue control signal when the value of the series of consecutive sensor signals changes, in particular decreases in a predetermined amount.

In a preferred embodiment the back scattered light has the same wavelength as the emitted wavelength but the back scattered light may also have a different wavelength or wavelength range compared with the emitted wavelength, for example caused by fluorescence. Biological tissues very often comprise a plurality of layers having different properties. The human skin for example comprises layers of different properties, such as the stratum corneum, which is the top layer, followed by the epidermis and the dermis.

Each of these layers has different properties. The stratum corneum for example doesn't allow passing substances of high molecular weight. It is therefore of utmost importance, when for example creating pores into the skin for administering a high molecular drug through the skin into the human body, to make sure to completely remove the stratum corneum of preferably every single pore before applying the drug onto the skin, to allow entering the drug into the human body. It is known that the epidermis and/or the dermis may for example comprise blood vessels and nerve ends. To prevent pain or bleeding, it is therefore desirable not to enter too deep into these layers when creating pores in the skin using a laser beam. On the other hand it turned out that the thickness of the stratum corneum varies significantly among individuals. Further it turned out that the moisture of the stratum corneum or other tissue layers that are exposed to the air vary significantly from summer to winter due to environment humidity changes. It is therefore a need to provide a reliable and preferably also fast and inexpensive device and method to detect skin layers, or more generally, to detect varying tissue properties. In a preferred embodiment the device and method is used to completely ablate the stratum corneum, but to leave the epidermis or dermis as much as possible. Therefore the embodiment according to the invention must be able to reliably, fast and accurately detect different skin layers during pore creation, which means during deepening the pore. For example, as soon as the pore is so deep that it reaches the epidermis, the embodiment according to the invention should recognise the transition of the pore ground into a new skin layer, so the poration may be stopped. Most preferably the embodiment according to the invention allows detecting the water content of the respective tissue on the pore ground, to clearly recognise various skin layers. One advantage of the measurement of water content is that the different skin layers may be reliably detected, most preferably independent of skin colours. The embodiment according to the invention may therefore be applied for all human races such a white or black people, to detect various skin layers during pore creating in their skin.

The device and method according to the invention allows recognising tissue properties when a biological tissue such as the skin is ablated using a laser beam. The level of laser energy is within a range that ablates the biological tissue.

The device according to the invention comprises a sensor arranged to receive back scattered light from the biological tissue, comprises a tissue controller that is coupled to the sensor to receive a sensor signal of the sensor, and comprises a tissue controller being configured to compare a series of at least two consecutive sensor signals and being configured to generate a tissue control signal when the value of the series of consecutive sensor signals changes in a predetermined way, e.g. decreases. In the most preferred embodiment the sensor receives the back scattered light of the laser beam ablating the skin, which means the treatment beam, and there is no other beam such as a probe beam to measure the skin layer properties. In the most preferred embodiment the sensor measures the intensity of the back scattered light. In the most preferred embodiment a plurality of repeated laser pulses are necessary to be directed into the same pore to deepen the pore and to completely ablate the stratum corneum, and if necessary the epidermis. The back scattered light of the laser beam is influenced by the respective tissue that was ablated by the laser beam, which means that the back scattered light contains information about tissue properties of the ablated tissue. Therefore tissue properties of the pore ground can be detected. By using a continuous laser system the detector could measure back scattered light continuously, and the continuous laser system could deflect the laser beam to a next spot of tissue when the intensity of back scattered light changes, e.g. decreases, until the desired skin layer is removed.

It has been found out that the back scattered light, in particular the intensity of the back scattered light depends on properties of the biological tissue. The human skin for example comprises layers of different water content, the stratum corneum having a water content of about 15-20%, the epidermis having a water content of about 60-70%, and the dermis having a water content of about 70-80%. It has been found out that water has the highest absorption coefficient at a wave length of about 3 pm, and an Er:YAG laser emits a laser beam with a wave length of about 2,95 pm. This preferred laser type emits a laser beam of which the back scattered light is highly sensitive to the water content of the ablated biological tissue. In a preferred embodiment the back scattered light of each laser pulse emitted into the same pore is measured by the sensor and at least two consecutive sensor signals are stored in a memory. As long as the stratum corneum is ablated by the laser beam, the sensor received a back scattered light of relative high intensity, due to the relative low water content of the stratum corneum. In a further preferred embodiment the sensor signal is at least sampled once within each laser pulse. The obtained time discrete pulse train, e.g. a series of signals, is further derivated to get information about the change of signal amplitude which is used to determine the tissue layer. As soon as the laser beam hits the epidermis, the intensity of the back scattered light decreases because the epidermis absorbs the laser beam more due to the relative high water content. The measurement of the reflected light therefore allows determining whether the laser pulse ablates biological tissue in the stratum corneum or the epidermis, and allows to clearly detect the transition from the stratum corneum to the epidermis in that a decrease in the intensity of the back scattered laser light occurs, which can be detected and measured by a sensor. In a preferred embodiment the ablation of the respective pore with a laser beam is stopped as soon as the epidermis is reached, for example to guarantee a pore with completely removed stratum corneum and small impact onto the epidermis. In another embodiment the ablation is stopped when the dermis is reached, so it also completely removes the epidermis. More generally the water content of the ablated tissue is determined during ablating the tissue, and the depth and the final depth of the ablation is controlled by monitoring the water content. Besides the skin, this concept is also suitable for other biological material, such as a finger nail, where for example the transition between the finger nail and the skin laying underneath the finger nail can clearly be detected. This concept is even suitable for bones, to detect the water content in bones, which may vary depending on the depth of a pore.

By way of example the device and method according to the invention has above been described in conjunction with porating the skin. But it is obvious that the device and method according to the invention may also be used to alter or ablate other biological tissue, thereby detecting properties of the biological tissue. The device and method may further be used in combination with pulsed laser beams as well as with continuous wave lasers.

One advantage of the device and method according to the invention is, that it is very inexpensive, very reliable, very fast, and allows to reliably detect changes in properties of the biological tissue, most preferably the water content of the tissue. In particular for a laser beam in the range of between 2.9 μm and 3 μm the intensity of the reflected laser beam depends on the water content of the tissue, wherein the tissue absorbs more intensity of the laser beam the more water the tissue contains, on the other hand the tissue reflects more of the intensity of the laser beam the less water the tissue contains.

The device and method according to the invention allows to use a laser having a wavelength in the range between 1.5 μm and 12 μm, more preferably in the range of between 2.5 μm and 3.5 μm, and most preferably in the range of between 2.9 μm and 3 μm.

In a further embodiment the device and method comprise a treatment beam and an additional source of illumination, a probe beam, which preferably is directed onto the area where tissue is ablated, and which preferably illuminates this area during and/or between two consecutive pulses, to receive back scattered and/or reflected light from the tissue containing information about tissue properties. In a preferred embodiment the source of illumination is a laser emitting light. Most preferably the laser emits a light in the wavelength range of 200 nm to 700 nm, whereby the wavelength is preferably selected to clearly distinguish smaller changes in tissue properties, such as the change from the epidermis to the dermis where e.g. the structure of the tissue changes and therefore it's optical characteristics.

A proper selection of the wavelength allows detecting the transition from the epidermis to the dermis.

As used herein, "poration" means the formation of a small hole or pore or a plurality of holes or pores to a desired depth in or through the biological membrane or tissue, such as the skin, the mucous membrane or an organ of a human being or a mammal, or the outer layer of an organism or a plant, to lessen the barrier properties of this biological membrane to the passage of permeants or drugs into the body. The poration referred to herein is preferably no smaller than 1 micron across and at least 1 micron in depth.

As used herein "ablation" means the controlled removal of material using a laser beam. As used herein, "biological tissue" means any component of an organism including but not limited to, skin, cells, biological membranes, bone, collagen, nails, blood vessels, fluids and the like comprising some portion of the organism.

As used herein "sensor" means any kind of radiation sensing or detecting devices including but not limited to photo diodes, photo resistors, photo transistors, thermopiles (e.g. lead sulfide, lead selenide) bolometric detectors, pyroelectric detectors (e.g. tourmaline, lithium-tantalate, triglycine-sulphate, polyvinyldentifluoride, polymers, gallium nitride, caesium nitrate, polyvinyl fluorides, derivatives of phenylpyrazine, cobalt phthalocyanine), ferroelectric detectors, piezoelectric detectors, photo multiplier tubes, CCD detectors and arrays.

As used herein "back scattered light" means reflected or deflected light that was sent to a tissue and is received through a sensor due to indirect or direct reflections caused on or in the tissue. This also includes receiving the light that is generated when using a first wavelength to stimulate an emission of an at least second wavelength on or in the tissue.

The term "individual pore" as used in the context of the present application refers to a pore, in general a pathway extending from the biological membrane. The biological membrane for example being the skin, the individual pore then extending from the surface of the skin through all or significant part of the stratum corneum. In the most preferred embodiment the pathway of the individual pore extending through all the stratum corneum and part of the epidermis but not extending into the dermis, so that no bleeding occurs. In the most preferred embodiment the individual pore having a depth between 10 μm (for newborns 5 μm) and 150 μm.

After the perforation a substance such as a drug is applied onto the skin, preferably in form of a transdermal patch.

In a preferred embodiment, at least two pulses of the laser beam are directed to the same pore. The deflector is built or controlled such that a second, third or even more laser beams are directed into the same pore. This multiple targeting of the same pore also allows using a laser beam of relative low energy. This makes sense because the maximum optical penetration depth is for example about 2 to 4 microns in human skin at wavelengths of about 3 microns. It is therefore very inefficient to create very deep pores of 70 to 200 microns with one single laser pulse. Such deep pores of 70 to 200 microns are needed for higher permeation rates of e.g. lipophilic and large hydrophilic permeants through the epidermis to the blood vessels in the dermis. The laser beam may be directed up to ten times or even up to fifty times into the same pore, whereby the beam is preferably directed consecutively into the same pore, to thereby "drilling" microholes into the biological membrane. The beam may also be redirected into a single one of a plurality of pores, after impacting at least one of the plurality of other pores.

In a preferred embodiment, the laser porator comprises a feedback loop based on back scattered light. In the most preferred embodiment, the feedback loop is continuously and operatively coupled to a poration controller that actuates the laser source. The poration controller compares the measured characteristic of an individual pore with a predetermined value and stops emitting further laser pulses on the individual pore if the characteristic of the individual pore corresponds to the preset value. Most preferred the depth of the individual pore is monitored. This allows creation of an individual pore similar to drilling a hole in a material, in that the depth of the hole e.g. the pore is repeatedly measured. The accuracy of the final depth of the individual pore can, for example, be improved if reduced laser energy is applied per pulse, which causes a smaller amount of biological tissue being ablated per pulse.

In one embodiment the width of the laser beam and/or the energy density of the laser beam can be modulated, which allows to modulate the width of the individual pore as well as the ablated depth per pulse.

The laser micro-porator preferably uses a laser source having a wavelength between 0.05 microns (micrometers) and 15 microns, preferably between 2 and 10 microns, in particular between 2.8 microns and 3.1 microns or 3.15 microns. Most preferred a wavelength of about 2.95 microns is used because the absorption maximum of water is in the mid infrared range, as disclosed in FIG. 14.

The laser micro-porator preferably uses an optical apparatus that generates a laser beam having a width between 0.05 and 0.5 mm or 1 mm. In a preferred embodiment the laser beam has a circular, elliptic or rectangular shape, the width of the circular laser beam being the diameter, the width of the rectangular laser beam being one of the lengths of the rectangle or ellipse.

The laser micro-porator preferably uses a laser source having a pulse temporal width which is between 1 ns and 1000 μs, in particular between 1 ns and 1 μs and most preferred between 10 ns and 50 ns or 50 ns and 150 ns.

The laser micro-porator also preferably uses a laser source having an energy density of the laser beam between 1 mJ/cm$^2$ and 100000 J/cm$^2$, in particular between 10 mJ/cm$^2$ and 5 J/cm$^2$.

BRIEF DESCRIPTION OF THE DRAWINGS

The present invention can be better understood and its advantages appreciated by those skilled in the art by referencing to the accompanying drawings. Although the drawings illustrate certain details of certain embodiments, the invention disclosed herein is not limited to only the embodiments so illustrated.

FIG. 10 shows a third ablator for ablating biological tissue in detail;

FIG. 11, 12 show a longitudinal section of tips pressed onto the skin;

FIG. 13 shows a tip pressed onto the finger nail;

DETAILED DESCRIPTION

Figure 1:
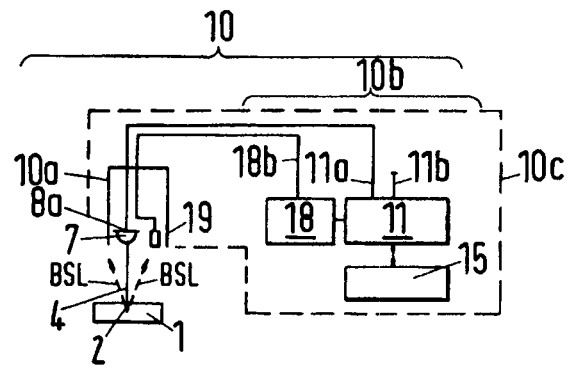
FIG. 1 shows a first ablator for ablating biological tissue.
Figure 20:
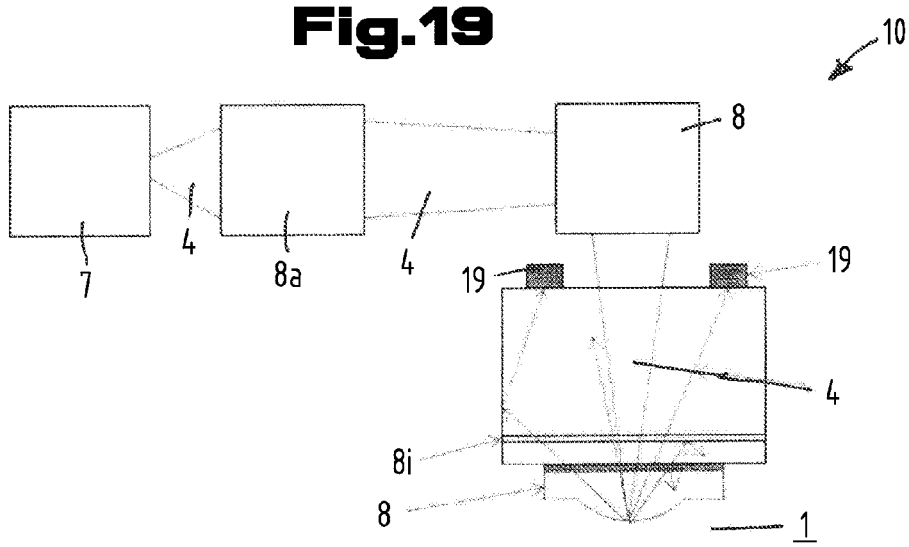
FIG. 20 shows a detail of a further ablator for ablating biological tissue, similar to FIG. 6.

FIG. 1 shows an ablator 10, which is a laser device 10 for ablating a biological tissue 1, comprising a laser source 7 that is configured to emit a laser beam 4, comprising optics 8a configured to modify the laser beam 4 such that the laser beam 4 has a diameter of preferably less than 1 mm, comprising a controller 11 that is configured to control the laser source 7 to emit the laser beam 4 to create an ablation 2 in the biological tissue 1, wherein a sensor 19 is configured to receive back scattered light BSL from the biological tissue 1. The ablator or laser device 10 disclosed in FIG. 1 comprises a hand piece 10a wherein the laser source 7 and the sensor 19 is arranged, and further comprises electronics 10b, in particular the controller 11, which is connected with a tissue controller 18 and an input-output device 15 or interfaces 15. The hand piece 10a and the electronics 10b communicate through connecting wires 11a, 18b. In a further preferred embodiment, parts 10a and 10b are arranged together in a common housing 10c. FIG. 20 shows a further embodiment of an ablator 10, similar to the one disclosed in FIG. 1. The ablator according to FIG. 20 comprising an ablation laser 4 emitting a laser beam 4, comprising optic 8a and a scanner 8 to direct the laser beam 4 onto the skin 1. There is a disposable scanner 8 having a housing and a protection window 8i. The laser beam 4 is reflected from the skin to the sensor 19.

Figure 2:
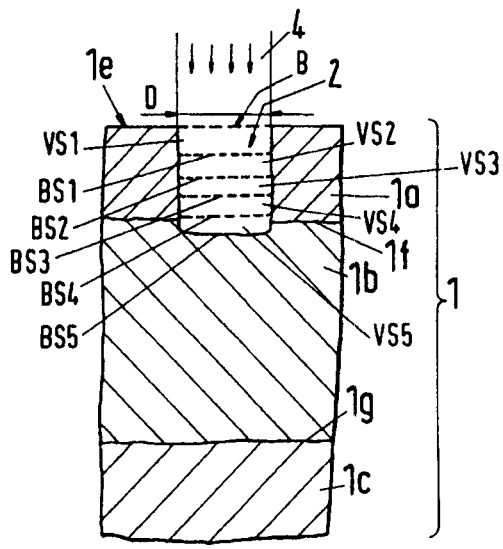
FIG. 2 shows a schematic cross-section of one pore of a laser porated skin.

In the most preferred embodiment, the ablator 10, respectively the laser source 7 emits a series of laser pulses. FIG. 2 shows a cross-sectional view of one pore 2 created in the skin 1 by using the ablator 10 disclosed in FIG. 1. The skin 1 comprises various tissue layers, of which the stratum corneum 1a, the epidermis 1b and the dermis 1c are shown. The ablator emits a consecutive series of laser pulses. The laser beam 4 is directed onto the surface 1e of the skin 1, and hits the skin surface 1e in the area B. The first shot S1 of the laser pulse ablates a tissue volume VS1, thereby after the first shot S1 of the laser pulse leaving a pore 2 with a bottom BS1. Further shots S2, S2, S3, S4, S5 of laser pulses follow, which ablate tissue volumes VS2, VS3, VS4, VS5 thereby creating a pore 2 with increasing depth, whereby the bottom BS2, BS3, BS4, BS5 of the pore 2 after each shot is indicated.

Each shot S1,S2,S3,S4,S5 of the laser beam 4 causes some back scattered emission originating from within the pore 2, such as part of the laser beam 4 being scattered back from the ablated tissue volume VS, the bottom BS of the pore 2, or the tissue below the bottom BS of the pore 2. The term "back scattered light" used herein means back scattered emission from a laser beam 4 or another emitting device, scattered back from the tissue, whereby the term light is not restricted to visible light but may also comprise electromagnetic emission of other wave length. The back scattered light is detected by sensor 19 and the received sensor signal Si is stored in the tissue controller 18.

The human skin 1 comprises different tissue layers, each tissue layer having a different water content, the stratum corneum 1a having a water content of about 15-20%, the epidermis 1b having a water content of about 60-70%, and the dermis 1c having a water content of about 70-80%. It has been found out that water has the highest absorption coefficient at a wave length of about 3 μm, and an Er:YAG laser emits a laser beam with a wave length of about 2.95 μm. An Er:YAG laser emitting a laser beam of about 2.95 μm is therefore very suitable to detect different tissue layers. This preferred laser emits a laser beam 4 of which the back scattered light is highly sensitive to the water content of the ablated biological tissue, therefore allowing to detect the water content of the ablated tissue. In a preferred embodiment the back scattered light of each laser pulse S1, S2, . . . emitted into the same pore 2 is measured by the sensor 19 and at least two consecutive sensor signals BSL1, BSL2, . . . are stored in a memory of the tissue controller 18.

Figure 3:
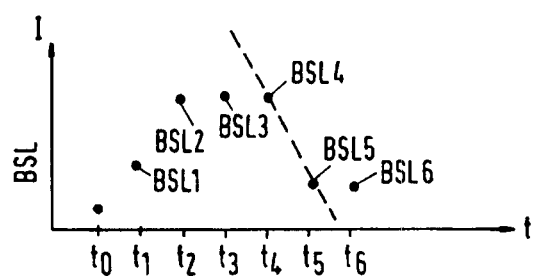
FIG. 3 shows a graph of the intensity of back scattered light versus time.

FIG. 3 shows a graph of the intensity of back scattered light versus time of the pore 2 created according to FIG. 2. As long as the stratum corneum 1a is ablated by the laser beam 4, the sensor 19 receives a back scattered light of relative high intensity, due to the relative low water content of the stratum corneum. Most preferred at least the first laser pulse S1 causes a dehydration of the tissue 1 surrounding the pore 2 and/or the tissue 1 below the respective bottom BS1, BS2, BS3, BS4, which reduces the water content of the tissue 1, and which therefore increases the intensity of back scattered light. This effect is shown in FIG. 3, where the intensity of back scattered light BSL1, BSL2 increases from shot 1 to shot 2, because the first shot 1 reduced the water content in the stratum corneum 1a, thereby effecting a lower absorption of the laser beam 4 on the bottom BS2, BS3, BS4 and therefore causing a higher intensity of back scattered light BSL2, BSL3, BSL4.

As soon as the laser beam 4 hits the epidermis 1b, the intensity of the back scattered light significantly decreases because the epidermis 1b absorbs the laser beam 4 more due to the relative high water content. The intensity of the back scattered light BSL5 therefore decreases in a predetermined amount. The tissue controller is configured to compare a series of at least two consecutive sensor signals BSL4, BSL5, and is configured to generate a tissue control signal TCS when the value of the series of consecutive sensor signals BSL4, BSL5 decreases in a predetermined amount. There are various ways to detect the decrease, for example by calculating the differential or the integral of the time series of the intensity of back scattered light. Therefore, the measurement of the back scattered light allows determining whether the laser pulse ablates biological tissue in the stratum corneum or the epidermis, and allows to clearly detect the transition from the stratum corneum to the epidermis in that a decrease in the intensity of the back scattered laser light is measured. As indicated in FIG. 2, in a preferred embodiment the ablation of the respective pore 2 with a laser beam 4 is stopped as soon as the epidermis 1b is reached, which means as soon as the tissue control signal TCS is generated, for example to guarantee a pore 2 with completely removed stratum corneum 1a and little impact onto the epidermis 1b.

The procedure described above has the advantage that the back scattered light originating from within the pore is measured, which therefore allows, even if the pore has a very small diameter of less than 1 mm, to clearly detect the tissue properties within the respective pore 2. In a preferred embodiment the back scattered light of the laser beam 4 is sufficient to detect tissue properties. Because no other light source is needed, the measurement is the back scattered light is very fast and very reliable, thus allowing a high pulse repetition frequency of for example 200 to 1000 Hz. A further advantage of the most preferred embodiment is that no calibration is necessary regarding different individual skins, such as the level of melanin in the skin, or such as black or white skin, because the detection method is based on the water content of skin layers and not on the visible colour of the skin.

Figure 18:
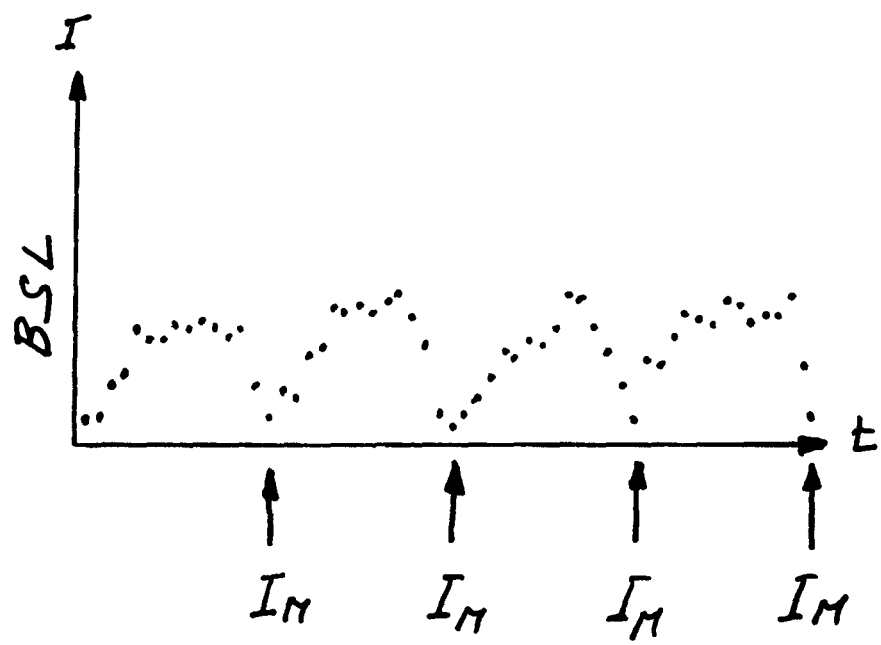
FIGS. 18 and 19 show further graphs of the intensity of back scattered light versus time.
Figure 19:
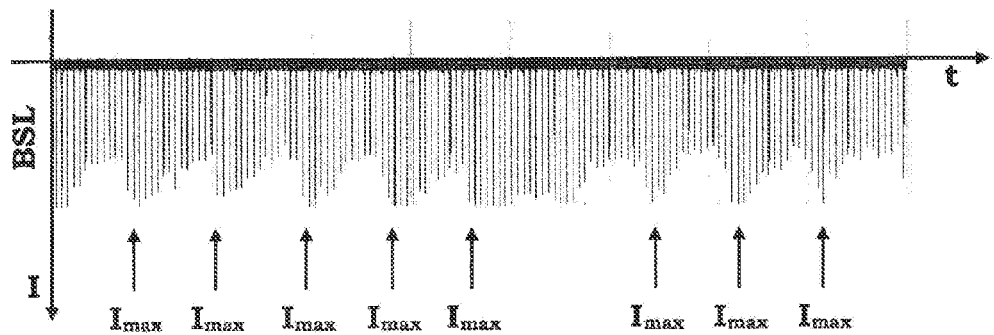

FIG. 18 shows another graph of the intensity of back scattered light versus time of a plurality of pores 2 created according to FIG. 2. The laser device is operated such that the stratum corneum 1a is completely ablated by the laser beam 4, by emitting a plurality of laser pulses 81 into the same pore 2, and that the laser beam 4 is directed onto another location to create a new pore 2 as soon as the epidermis 1 b is reached. Beginning on the left side of the time axis t, the laser beam 4 is directed onto the same location to create a pore 2, whereby each dot represents the intensity of the reflected light of a laser pulse. Analogous to the graph according to FIG. 3, the intensity of the reflected light according to FIG. 18 first increases, due to the relative low water content of the stratum corneum. As soon as the epidermis Ibis reached the intensity of the reflected light significantly decreases, due to the relatively high water content of the epidermis 1 b, what causes the laser beam to be absorbed in the epidermis 1 b. The reach of the epidermis 1 b can, for example, be detected by the sharp decrease of the intensity. The last laser pulse directed into the same pore 2 is indicated by 1M. Because the epidermis Ibis now reached, the laser beam 4 is directed onto another location and the laser pulse following the pulse indicated by 1M therefore starts to create a new pore 2 in the biological tissue. As indicated in FIG. 18 a series of laser pulses are directed into the same pore 2, until the epidermis Ibis reached, which is indicated by the next 1M. This procedure is continued until all pores 2 are created. The example disclosed in FIG. 18 shows the creation of four pores 2, wherein the laser beam is directed onto a new location creating a new pore 2 after each laser pulse indicated with 1M. This procedure has the advantage that it ensures that the complete stratum corneum has been ablated in each pore 2. A further advantage is that the depth of each pore 2 is only as deep as necessary to completely remove the stratum corneum and to reach the epidermis 1b, therefore avoiding pain and allowing the pore 2 very soon to be covered with stratum corneum again. It is important to understand that the thickness of the stratum corneum depends on various intraindividual and interindividual factors, which means that it is not possible to just ablate a certain thickness of the stratum corneum, e.g. 0.2 mm, to be sure the stratum corneum is ablated. Only by detecting tissue properties when deepening the pore it is possible to clearly detect when the stratum corneum ends, respectively when the epidermis starts. Each pore 2 may need a different number of laser pulses to completely remove the stratum corneum, which can very easily be achieved by the procedure according to the invention. A similar procedure as described above could be used to create pores 2 with completely removed epidermis 1b, whereby the pores 2 are only as deep as necessary to reach the dermis 1c. The transition from the epidermis 1b to the dermis 1c in pore 2 can also be detected, as disclosed in FIG. 18, by detecting a laser pulse with minimum reflected intensity, because the dermis 1c has a relatively high water content and therefore causes a reflected laser pulse with low intensity. This procedure may also be used for other tissues containing water, even for bones, containing just little water.

Figure 4:
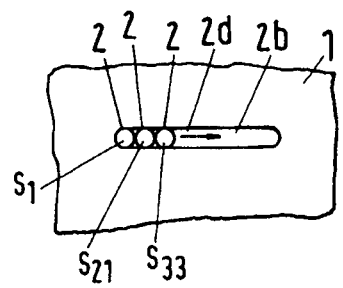
FIG. 4 shows a top view of a cut in the skin created with the ablator.
Figure 5:
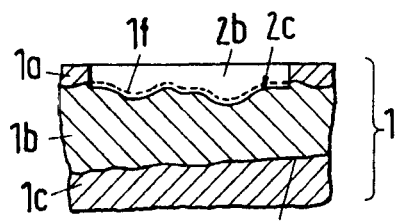
FIG. 5 shows a longitudinal section of the cut in the skin according to FIG. 4.

The ablator 10 disclosed in FIG. 1 may for example be used to cut a tissue up to a depth with predetermined tissue properties. FIG. 4 shows a top view of the skin 1, along which the ablator 10 according to FIG. 1 is moved with a scanner or manually in direction 2d. Assuming the ablator 10 being fixed on a scanner moveable in direction 2d, the ablator 10 emits a first shot S1, creating a pore 2 of little depth. The ablator 10 emits a series of shots into the pore 2, thereby measuring the back scattered light after preferably each shot Si. Lets assume that after twenty shots in total, the bottom of the pore 2 reaches the epidermis b1, which causes the tissue controller 18 to emit the tissue control signal TCS, and the consecutive series of shots is stopped, until the scanner has moved the ablator 10 to such a position, that the next shot 21 will hit the skin 1 just beside the previously created pore 2. After a total shot number of 22, a further tissue control signal TCS is issued, and the scanner moves the ablator 10 to such a position, that the next shot number 33 will hit the skin 1 just beside the previously created pore 2. This procedure is continued until the whole incision 2b is created. FIG. 5 shows a longitudinal section of the incision 2b created in the skin 1 according to FIG. 4. As indicated the thickness of the stratum corneum 1a may vary. There is a border 1f between the stratum corneum 1a and the epidermis 1b. The method described above allows, for example to create an incision 2b having a depth 2c of little more than the thickness of the stratum corneum, so that the stratum corneum is completely removed with the incision 2b, but most of the epidermis 1b is left.

Figure 6:
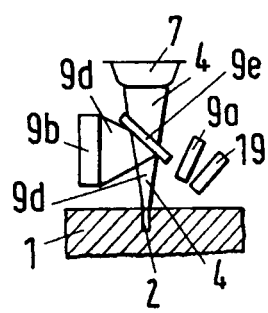
FIG. 6 shows a detail of a second ablator for ablating biological tissue.
Figure 21:
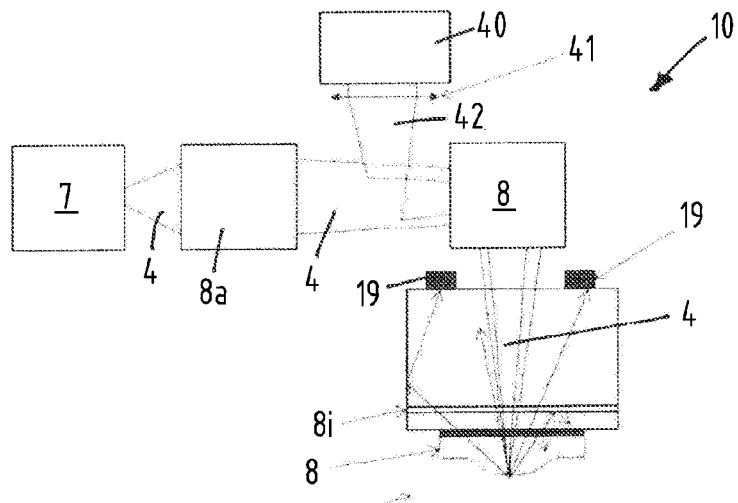
FIG. 21 shows a further ablator for ablating biological tissue.

FIG. 6 shows a schematic detail of a second ablator 10 for ablating biological tissue. This ablator 10 comprises all embodiments disclosed in FIG. 1, in particular the laser 7 and the sensor 19. In addition to the first ablator 10, the second ablator 10 according to FIG. 6 comprises also a beam splitter 9e and a sensor 9b, whereby the sensor 9b and the beam splitter 9e are configured to receive light of the laser beam 4, back scattered of pore 2. This arrangement allows to even more reliably detect back scattered light of pore 2. FIG. 21 shows a very similar arrangement as that of FIGS. 6 and 20. In addition to the embodiment according to FIG. 20, the embodiment according to FIG. 21 comprises an additional laser module 40, for example a green laser module, and comprising a focusing lens 41, to direct the laser beam 42 onto the scanner 8, which directs both laser beams 4 and 42 into a pore of the skin 1. Part of the laser beams 4 and 42 are back scattered to the sensors 19, so the back scattered light of the green laser module 40 can be measured by sensors 19.

In a further embodiment, an additional light source 9a may be used, whereby the light source 9a is arranged so that sensor 9b or sensor 19 receives light of light source 9a back scattered by the pore 2. Most preferably the light source 9a emits light, which is back scattered by pore 2, and emitted as beam 9d onto the sensor 9b. Preferably the wave length of light source 9a differs from the wave length of laser beam 4. The light source 9a, most preferably a laser source, may for example emit green light in the range of for example 530+/−20 nm; or blue light in the range of for example 400+/−30 nm, or red light in the range of for example 630+/−30 nm. The wave length of the light source 9a is for example of importance to detect tissue of different properties. Depending on spectral tissue properties usually a specific wave length, properly selected, allows detecting different tissues with an arrangement as disclosed in FIG. 6.

Figure 7:
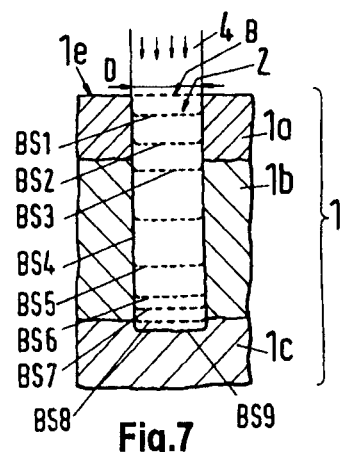
FIG. 7 shows a schematic cross-section of another pore of a laser porated skin.

For example FIG. 7 shows a cross section of a pore 2 in a laser porated skin 1. After 9 shots the bottom line BS9, which means the dermis 1c is reached. The epidermis 1b has a water content of about 60-70%, whereas the dermis 1c has a water content of about 70-80%. To clearly recognise the dermis layer 1c using the embodiment disclosed in FIG. 6, the light source 9a used is a blue laser. The back scattered light is received by sensor 9b and the measured sensor signal transmitted to the tissue controller 18. As soon as the value of the series of consecutive sensor signals decreases in a predetermined amount, the tissue controller 18 generates a tissue control signal TCS, indicating that the dermis 1c has been reached. After the tissue control signal TCS is generated, the ablator 10 stops issuing laser pulses 4, or the laser beam 4 is directed onto another location.

Figure 8:
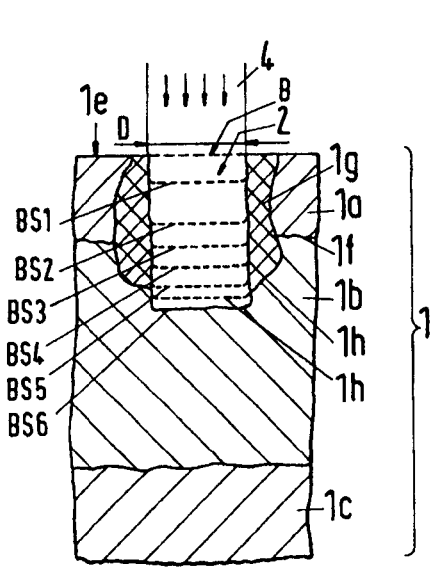
FIG. 8 shows a schematic cross-section of another pore of a laser porated skin.

The embodiment according to FIG. 6 allows detecting various different tissues. The schematic cross-section of FIG. 8 shows an undesirable tissue 1g within the stratum corneum and partly within the epidermis 1b. This undesirable tissue 1g may for example be an alteration in the skin such as a tumor or a tattoo. The method and apparatus according to FIG. 1 or 6 allows to create a pore 2 of such depth, that by shot number 6 a bottom wall BS6 is created, being a little deeper than the border line 1h between the undesirable tissue 1g and the epidermis 1b. The tissue controller 18 recognises the tissue of the epidermis 1b and therefore allows to stop the laser beam 4. This allows automatically creating a pore 2 as deep as necessary to remove the undesirable tissue 1g. Two further pores 2 are created on the left and right side of the remaining undesirable tissue 1g, to completely remove the undesirable tissue 1g.

Figure 9:
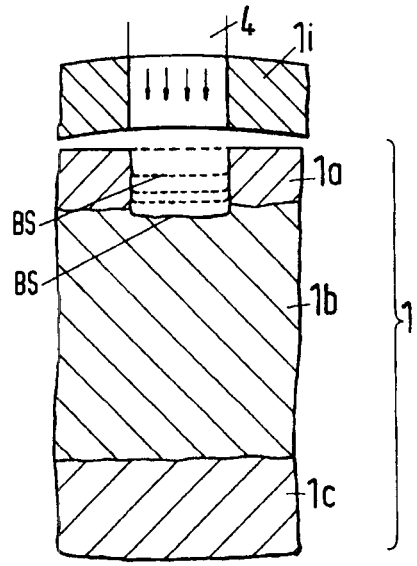
FIG. 9 shows a schematic cross-section of another pore of a laser porated fingernail and finger.
Figure 14:
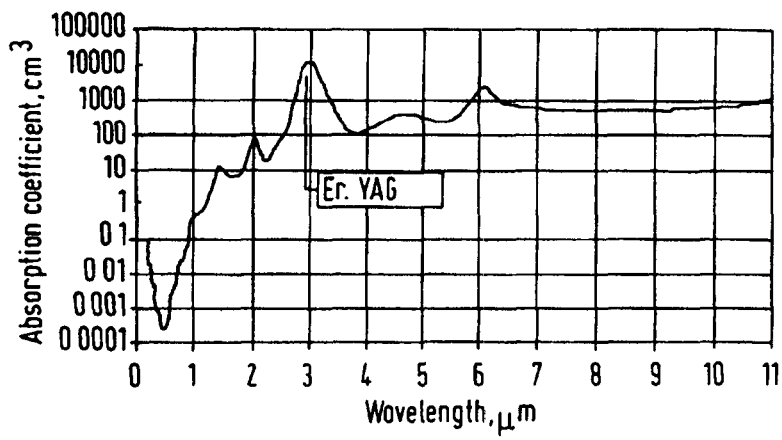
FIG. 14 shows a graph of the absorption coefficient of water versus wavelength.

The device and method according to the invention allows porating a wide variety of different tissues. FIG. 9 shows a partial cross-section of a finger with a finger nail 1i. The device and method according to the invention allows for example detecting the end of the finger nail 1i, or the beginning or end of the stratum corneum 1a, which allows creating pores penetrating predetermined tissue layers. In might be advantageous not to enter the epidermis 1b of the skin 1 below the finger nail 1i, because this epidermis 1b contains nerve ends, which would cause pain, if the created pore 2 would penetrate as deep as the epidermis 1b.

FIG. 10 shows a laser micro-porator 10 comprising a Q-switched laser source 7 and a laser beam shaping and guiding device 8. The laser source 7 has a light source 7c for optical excitation of a laser active material 7b, and a set of reflecting mirrors 7d, 7e. The laser source 7 comprises a laser cavity 7a containing a laser crystal 7b, preferably Er and optional additionally Pr doped YAG, which is pumped by an exciter 7c, the exciter 7c being a single emitter laser diode or a set of single emitter laser diode arrays like emitter bars or stacks of emitter bars. The laser source 7 further comprising an optical resonator comprised of a high reflectance mirror 7d positioned posterior to the laser crystal 7b and an output coupling mirror 7e positioned anterior to the laser crystal 7b, and a saturable absorber 7f positioned posterior to the laser crystal. The saturable absorber 7f works as a Q-switch. A focusing lens 8a and a diverging lens 8b are positioned beyond the output coupling mirror 7e, to create a parallel or quasi-parallel laser beam 4 or a focused laser beam 4. Instead of the lenses 8a, 8b, the microporator 10 could comprise different optical means 8a, 8b, which, for example, focus the laser beam 4 onto the surface of the skin 1. The diverging lens 8b can be moved by a motor 8c in the indicated direction. This allows a broadening or narrowing of the laser beam 4, which allows changing the width of the laser beam 4 and the energy fluence of the laser beam 4. A variable absorber 8d, driven by a motor 8e, is positioned beyond the diverging lens 8b, to vary the energy fluence of the laser beam 4. A deflector 8f, a mirror, driven by an x-y-drive 8g, is positioned beyond the absorber 8d for directing the laser beam 4 in various directions, to create individual pores 2 on the skin 1 on different positions. A control device 11 is connected by wires 11a with the laser source 7, drive elements 8c, 8e, 8g, sensors and other elements not disclosed in detail.

In a preferred embodiment the laser porator 10 also includes a feedback loop 13 respectively a feedback mechanism. In FIG. 10, the feedback loop 13 comprises a sender 9a with optics that produce a laser beam 9d, and a receiver with optics 9b. The laser beam 9d may have a smaller width than the diameter of the individual pore 2, for example five times smaller, so that the laser beam 9d can reach the lower end of the individual pore 2. The deflection mirror 8f directs the beam of the sender 9a to the individual pore 2 to be measured, and guides the reflected beam 9d back to the receiver 9b. This measurement device 9, which can be built in different way, allows measuring properties of the lower end e.g. the water content of the respective tissue. In a preferred embodiment, properties of the individual pore 2 are measured each time after a pulsed laser beam 4 has been emitted to the individual pore 2, allowing controlling the effect of each laser pulse onto the depth of the individual pore 2. The feedback loop 13 can be built in various ways to be able to measure a feedback signal of an individual pore 2. The feedback loop 13 may, for example, comprise a sender 9a and a receiver 9b, built as a light intensity measurement device, or as a spectrograph 14, to detect changes in the intensity or spectrum of the light reflected by the lower end of the individual pore 2. This allows, for example, detecting whether the actual lower end 3a, 3b, 3c, 3d of the individual pore 2 is part of the stratum corneum 1a or of the epidermis 1b. The laser porator 10 also comprises a poration memory 12 containing specific data of the individual pores 2, in particular the initial microporation dataset. The laser porator 10 preferably creates the individual pores 2 as predescribed in the poration memory 12. The laser porator 10 also comprises one or more input-output device 15 or interfaces 15, to enable data exchange with the porator 10, in particular to enable the transfer of the parameters of the individual pores 2, the initial microporation dataset, into the poration memory 12, or to get data such as the actual depth or the total surface Ai of a specific individual pore 2i. The input-output device 15 can be a card reader, a scanner, a wired interface or for example a wireless connection such as Bluetooth.

The porator further can comprise one or more input-output devices or user interfaces 15 for manually exchange date like data of substances, individuals and much more. The user interface can for example comprise displays, buttons, voice control or a finger print sensor.

There are different ways to build a laser source 7. The laser source 7 may, for example, be built as a laser diode with optics that create a beam 4 of fixed width, for example a width of 250 μm. The Laser source 7 can advantageously also comprises an absorber 8d. In a simple version, the laser porator 10 can only comprise the laser source 7 with a built in lens system, and a deflection mirror 8f for direction the laser beam 4 in various directions. Instead of the absorber 8d, the intensity of the laser beam 4 can directly be modulated by driving the laser diode 7 accordingly.

The pulse repetition frequency of the laser source 7 is within a range of 1 Hz to 1 MHz, preferably within 100 Hz to 100 kHz, and most preferred within 500 Hz to 10 kHz. Within one application of the laser porator 10, between 2 and 1 million individual pores 2 can be produced in the biological membrane 1, preferably 10 to 10000 individual pores 2, and most preferred 10 to 1000 individual pores 2, each pore 2 having a width in the range between 0.05 mm and 0.5 mm or up to 1 mm, and each pore 2 having a depth in the range between 5 μm and 200 μm, but the lower end of the individual pore 2 being preferably within the epidermis 1b. If necessary the porator 10 is also able to create pores of more than 200 μm depth.

The laser porator 10 may also comprise an interlock mechanism, so that a laser pulse is emitted only when it is directed onto the skin 1. The feedback loop 13 could for example be used to detect whether the pulse is directed onto the skin 1. Those skilled in the art will appreciate that there are numerous ways to create an interlock mechanism, and all such ways are contemplated.

The water content of the individual pore 2 can be measured before and after applying a laser pulse, and due to the fact that the stratum corneum, the epidermis and the dermis have different properties, for example a different amount of water, and depending on the change of the amount of the ablation per applied laser pulse, if the same energy per pulse is used, one can determine whether the lower end of the pore is in the stratum corneum, the epidermis or the dermis. In a preferred embodiment, the thickness of the stratum corneum 1a, or if necessary the epidermis 1b can be determined based, on information about the change of the amount of the ablation in depth per pulse. In another embodiment the tissue layers can be differentiated with spectroscopic means.

FIG. 10 discloses a circular laser beam 4 creating a cylindrical individual pore 2. The individual pore 2 can have other shapes, for example in that the laser beam 4 has not a circular but an elliptical shape, a square or a rectangle. The individual pore 2 can also be shaped by an appropriate movement of the deflector 8f, which allows creation of individual pores 2 with a wide variety of shapes.

FIG. 11 shows a tip 8 pressed onto the skin 1, the tip 8 having a convex tissue biasing element 8a. Most preferably the curvature of the tissue biasing element 8a is adapted to deflect the skin 1 such that preferably all deflected laser beams 4,4a,4b, ... hit the skin 1 at about the same point of focus, which allows to hit the skin 1 with a laser beam 4 or a laser pulse with similar energy. This allows creating a plurality of pores 2 with reproducible shape and properties. FIG. 12 shows another tip 8 pressed onto the skin 1. Tip 8 comprises a planar tissue biasing element 8a as well as an F-Theta lens 8i. As disclosed the F-Theta lens 8i causes the various deflected laser beams 4, 4a, 4b to hit the skin at a defined point of focus. FIG. 13 shows another tip 8 pressed onto the finger nail 1e of a finger 1d. The tip 8 comprises a concave tissue biasing element 8a adapted to the shape of the finger nail. The tip 8 comprises an optical path correction element 8i which is adapted such that the deflected laser beams 4, 4a, 4b hit the finger nail 1e with their focal point. A person skilled in the art understands how to adopt and choose an optical path correction element (for example shape, refraction index, thickness and so on) such that the deflected laser beam 4,4a,4b is focused on the tissue hit by the laser beam 4,4a,4b, also when the tissue biasing element 8a has a planar, convex or concave shape. The optical path correction element 8i may be part of the tip 8, but most preferably the optical path correction element 8i is part of the laser porator 10, so the same optical path correction element 8i can be used many times. A finger nail of a human being contains about 5 to 15% of water. The nail bed beneath the finger nail contains about 25% to 60% of water. The method according to the invention therefore allows to clearly determine when the deepening pore reaches the nail bed, so as to stop porating the pore as soon as the nail bed is reached. The nail bed contains blood vessels and nerves. It is therefore advantageous to stop porating as soon as the nail bed is reached, to avoid bleeding and pain.

Figure 15:
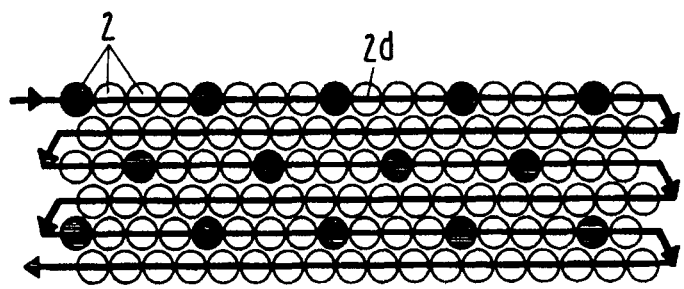
FIG. 15 shows the path of a series of laser pulses applied onto the biological tissue to ablate an area.

FIG. 10 discloses a deflector 8f which allows creating a plurality of pores 2 in a biological tissue. FIG. 4 discloses a scanner able to move the laser beam 4 in such a way on the skin 1, that an incision, for example along a straight line, may be created. Similar, the laser device 10 disclosed in FIG. 1 allows creating a path 2d of pores 2, as disclosed in FIG. 15, the individual pores 2 laying one beside the other, leaving no side wall between consecutive pores 2. The path 2 indicates by example about how the pores 2 may be ablated to create a whole area of ablated tissue. The device and method according to the invention therefore allows, for example, to completely remove the stratum corneum of a predetermined area of the skin 1, while not or only very little removing the epidermis. FIG. 5 discloses such a removal of the stratum corneum only for a two dimensional incision. The method disclosed in FIG. 15 allows a three dimensional removal of the stratum corneum. In a further method to operate the laser device, it might be advantageous to measure reflected of the pore 2 not for each consecutive pore, but only after a view pores 2 are created without measuring reflected light. In the method disclosed in FIG. 15, for example only for the pores 2 displayed in black back scattered light is measured to detect a tissue layer. Assuming that for the first black pore 2, 15 laser pulses 4 were needed to completely remove the stratum corneum, it can therefore be assumed that the next pore 2, arranged just beside the created pore 2, has similar properties, so that the same amount of 15 laser pulses is applied.

Figures 16, 17:
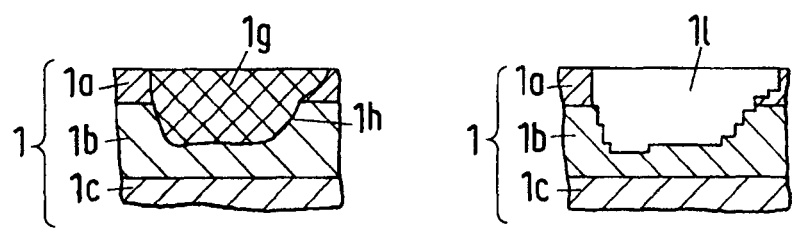
FIG. 16 shows a longitudinal section of the skin containing a defect tissue.
FIG. 17 the section according to FIG. 16 after ablating the defect tissue.

The device according to FIG. 10 may also be suitable to remove undesirable tissue 1g, for example from within the skin 1. FIG. 16 shows a longitudinal section of the skin 1 with an undesirable tissue 1g. FIG. 17 shows the same longitudinal section of the skin 1 with the removed undesirable tissue 1g. The undesirable tissue 1g was of three dimensional shape and could be completely removed, thereby destroying the healthy tissue as little as possible, and leaving a hole 11 in the skin 1. The consecutive series of individual pores 2 created by the method according to the invention can be recognised in that bottom of the hole 11 showing steps. The steps are formed by the bottom line of the respective pore 2, and the total of the ablated pores 2 leaving a bottom area in the hole 11 showing these steps.

Even though only ablation of the skin is disclosed in the previous figures, the method and device can be used for detecting tissues of different properties in a wide variety of biological tissues, and is therefore not restricted to the skin.

To recognize properties of the tissue within a pore 2, also a two-dimensional sensor may be used, the sensor receiving back scattered light from the skin and the pore, and the skin and the pore being illuminated, for example by a light source. As soon as the pore depth reaches the epidermis, the pore becomes very dark, because the high water content of the epidermis omits the reflection of the light. Further because the laser beam dehydrates tissue, there is a strong contrast between the tissue not being directly hit by the laser beam but being dehydrated, this tissue highly reflecting the light due to the effect that the tissue is dried. The properties of the pores, respectively the skin within the pore, may be recognized using a two dimensional sensor to receive back scattered light from the pore and the surface of the skin. As soon as a pore becomes very dark on the sensor, this indicated that the pore reached the epidermis. There is a plurality of known methods for two dimensional picture analysis, which would be suitable to be used for the detection of pores, and in particular for the detection that the pore reached a different tissue layer such as the epidermis or dermis.

The invention claimed is:

1. A laser device for ablating a biological tissue, comprising:
    a laser source that is configured to emit a laser beam in a series of at least two consecutive pulses with a repetition rate within 200 Hz and 1 kHz to a first location to create a pore with increasing depth;
    optics configured to modify the laser beam to direct the laser beam on the biological tissue in a direction that is parallel to a back scattered light of the laser beam from the biological tissue;
    a poration controller configured to control the laser source to emit the laser beam to create an ablation in the biological tissue;
    a sensor configured to receive and measure an intensity of back scattered light of the laser beam from the biological tissue;
    a tissue controller that is operationally coupled to the sensor to receive a time discrete pulse train of at least two consecutive sensor signals from the sensor representative of the intensity of back scattered light of the laser beam; and
    wherein the tissue controller is configured to calculate the differential or the integral of the time discrete pulse train of at least two consecutive sensor signals during creation of the pore and generate a tissue control signal when a value of the time discrete pulse train of at least two consecutive sensor signals decreases in a predetermined amount associated with a water content transition between a first skin layer and a second skin layer
    the tissue controller being configured to modify at least one of intensity, diameter, moving direction and moving speed of the laser beam, based on the tissue control signal.

2. The laser device of claim 1, further comprising:
    a deflector in various directions; and
    wherein the poration controller is further configured to control the deflector to create a poration comprising a plurality of individual pores, and further configured to direct the pulses to impact a single one of the plurality of pores at least twice.

3. The laser device of one of claim 1 or 2, wherein the tissue controller is configured to modify at least one of intensity and diameter of the laser beam emitted onto the first location of the biological tissue, based on the tissue control signal.

4. The laser device of claim 1, further comprising:
a deflector configured to direct the laser beam in various directions;
the poration controller being configured to control the deflector to move the laser beam along the biological tissue.

5. The laser device of claim 1, wherein the sensor is at least partially disposed within the laser device.

6. The laser device of claim 1, further comprising a removable tip, wherein the sensor is arranged in the removable tip.

7. The laser device of claim 1, wherein the sensor is configured to measure light intensity only.

8. The laser device of claim 1, wherein a wavelength of the laser beam is in the range of between 1.5 μm and 12 μm.

9. The laser device of claim 2, wherein the tissue controller is further configured to control the sensor to measure back scattered light of the laser beam.

10. A method for ablating a biological tissue, comprising the steps of:
emitting a laser beam from the laser device of claim 1 in a series of at least two consecutive pulses with a repetition rate within 200 Hz and 1 kHz to a first location to create a pore on a biological tissue with increasing depth;
directing the laser beam on the biological tissue in a direction that is parallel to a back scattered light of the laser beam from the biological tissue;
controlling the laser beam to create an ablation of the biological tissue;
measuring an intensity of back scattered light of the laser beam received from the biological tissue within each of the at least two consecutive pulses to obtain a time discrete pulse train of at least two consecutive sensor signals representative of the intensity of back scattered light of the laser beam; and
calculating the differential or the integral of the time discrete pulse train of at least two consecutive sensor signals during creation of the pore, and generating a tissue control signal when a value of the time discrete pulse train of at least two consecutive sensor signals decreases in a predetermined amount associated with a water content transition between a first skin layer and a second skin layer occurs and modifying at least one of intensity, diameter, moving direction and moving speed of the laser beam, based on the tissue control signal.

11. The method according to claim 10, wherein light intensity only is measured.

12. The method according to one of claims 10 and 11, wherein the laser beam is stopped and directed onto another area when a tissue control signal is generated.

* * * * *